(12) United States Patent
Ma et al.

(10) Patent No.: US 8,491,867 B2
(45) Date of Patent: Jul. 23, 2013

(54) METHOD OF NUCLEAR MEDICAL PHOTOGRAPHY USING DUAL-ISOTOPES

(75) Inventors: Kuo-Hsing Ma, Taipei (TW); Wen-Sheng Huang, Taipei (TW); Chia-Chieh Chen, Longtan Township, Taoyuan County (TW); Lie-Hang Shen, Zhongli (TW)

(73) Assignee: Atomic Energy Council-Institute of Nuclear Energy Research, Lungtan, Taoyuan (TW)

( * ) Notice: Subject to any disclaimer, the term of this patent is extended or adjusted under 35 U.S.C. 154(b) by 343 days.

(21) Appl. No.: 12/823,688

(22) Filed: Jun. 25, 2010

(65) Prior Publication Data

US 2011/0038796 A1     Feb. 17, 2011

(30) Foreign Application Priority Data

Aug. 13, 2009    (TW) ................................ 98127205 A

(51) Int. Cl.
     *A61K 51/04*        (2006.01)
     *A61K 51/00*        (2006.01)

(52) U.S. Cl.
     USPC ....... 424/1.85; 424/1.11; 424/1.45; 424/1.65; 424/9.1

(58) Field of Classification Search
     USPC .................... 424/1.11, 1.65, 1.81, 1.85, 1.89, 424/9.1
     See application file for complete search history.

(56) References Cited

PUBLICATIONS

Kuo-Hsing Ma et al. Simultaneous [99Tc] TRODAT-1 and [123I]ADAM Brain SPECT in Nonhuman Primates, Molecular Imaging Biology, 2009, 11, 253-262.*
Wen-Sheng Huang et al. 123I-ADAM SPECT in Healthy Nonhuman Primates: A Preliminary Report, Ann Nucl. Med Sci 2002, 15, 27-32.*

* cited by examiner

*Primary Examiner* — Michael G Hartley
*Assistant Examiner* — Jagadishwar Samala
(74) *Attorney, Agent, or Firm* — Jackson IPG PLLC

(57) ABSTRACT

A method of single photon emission computed tomography (SPECT) using dual-isotopes of [$^{99m}$Tc]TRODAT-1 and [$^{123}$I]ADAM is provided. Through SPECT, anomalies in dopamine and serotonin system are diagnosed with their photos in one examination. Thus, cost and labor for two examinations are saved and uses of SPECT are reduced.

3 Claims, 16 Drawing Sheets

METHOD OF NUCLEAR MEDICAL PHOTOGRAPHY USING DUAL-ISOTOPES

CROSS REFERENCE TO RELATED PATENT APPLICATIONS

This application claims priority from Taiwan Patent Application No. 098127205, filed in the Taiwan Patent Office on Aug. 13, 2009, entitled "Method of Nuclear Medical Photography Using Dual-Isotopes," and incorporates the Taiwan patent application in its entirety by reference.

TECHNICAL FIELD OF THE DISCLOSURE

The present disclosure relates to is nuclear medical photography; more particularly, relates to evaluating effect of single photon emission computed tomography (SPECT) on diagnosing anomaly of dopamine or serotonin system in brains of primates by using dual-isotopes, where photos of dopamine and serotonin system are obtained in one examination.

DESCRIPTION OF THE RELATED ARTS

Radiopharmaceuticals are used in nuclear medicine for imaging. Only a tiny quantity is needed for diagnosing living body with physiological and function image. Thus, they are used in clinical diagnosis and follow-ups after recovery for further treatment of some diseases like Alzheimer's disease, Parkinson's disease, etc.

The existence of receptors is related to the pathological depravation of related organs. Hence, pharmaceutical studies on inducing or eliminating functions of the receptors are crucial for inventing new drugs. Among them, nuclear medicine uses radioactive nuclei to trace biophysical and biochemical responses by finding numbers and positions of the receptors, where isotopes are labeled in various agents that can bind onto receptors or transporters. This is the only non-invasive way for receptor researches on a living body. Therein, anomalies of dopamine transporter (DAT) and serotonin transporter (SERT) have close relationship to many psychoneurotic symptoms and neurologic diseases. If situation of the dopamine transporter and the serotonin transporter in brain are clearly known, further treatment to the patient can be obtained with the situation information.

Radioactive developers used in nuclear medicine for dopamine transporter include [$^{123}$I]Altropane, [$^{123}$I]IPT, [$^{99m}$Tc]TRODAT-1, etc., where [$^{99m}$Tc]TRODAT-1 is the fastest in pharmacodynamics by reaching the highest binding level within two hours after injection. Radioactive developers used in nuclear medicine for serotonin transporter include [$^{123}$I]β-CIT, [$^{123}$I]nor-β-CIT, [$^{123}$I]ADAM, etc., where [$^{123}$I]ADAM has the best affinity to serotonin transporter and its affinity to serotonin transporter is 50-thousand times to those to other monoamine transporters like dopamine transporter and norepinephrine transporter.

However, regardless of the advantages of [$^{99m}$Tc]TRODAT-1 and [$^{123}$I]ADAM, photos of the two systems of dopamine and serotonin are obtained for diagnosis separately, including a photo by using a single-isotope of [$^{99m}$Tc]TRODAT-1 and another photo by using a single-isotope of [$^{123}$I]ADAM. This causes some problems. Decays of the isotopes have to be considered; and. a duration time between two system checks is required. Concerning patient position alignment, psychiatric patients may not be able to lie down peacefully, not to mention difficulties in discriminating photos taken at two positions in two times. Furthermore, patients having diseases like Parkinson's disease may be disabled in walking and so two times of come-and-go to hospital become a great bother. Hence, the prior arts do not fulfill all users' requests on actual use.

SUMMARY OF THE DISCLOSURE

The main purpose of the present disclosure, is to obtain photos of dopamine and serotonin system in one examination.

The second purpose of the present disclosure is to evaluating effect of SPECT using dual-isotopes on diagnosing anomaly of dopamine or serotonin system in brains of primates.

The third purpose of the present disclosure is to save cost and labor for two examinations and uses of SPECT.

To achieve the above purposes, the present disclosure is a method of nuclear medical photography using dual-isotopes, comprising steps of: (a) obtaining a control group, comprising a first individual applied with [$^{99m}$Tc]TRODAT-1; a second individual applied with [$^{123}$I]ADAM; and a third individual applied with [$^{99m}$Tc]TRODAT-1 and [$^{123}$I]ADAM; (b) obtaining photos of the first to the third individuals through SPECT; (c) processing visual interpretation to obtain a first specific uptake ratio (SUR) of [$^{99m}$Tc]TRODAT-1 ([$^{99m}$Tc]TRODAT-1 SUR) of the first individual; a first [$^{123}$I]ADAM SUR of the second individual; a second [$^{99m}$Tc]TRODAT-1 SUR of the third individual; and a second [$^{123}$I]ADAM SUR of the third individual, and comparing the second [$^{99m}$Tc]TRODAT-1 SUR and the second [$^{123}$I]ADAM SUR with the first [$^{99m}$Tc]TRODAT-1 SUR and the first [$^{123}$I]ADAM SUR; (d) obtaining a treatment group, comprising a fourth individual applied with [$^{99m}$Tc]TRODAT-1 and [$^{123}$I]ADAM after pretreated with methylphenidate HCl and fluoxetine separately; (e) obtaining photos of the fourth individual through SPECT separately; and (f) processing visual interpretation to obtain a third [$^{99m}$Tc]TRODAT-1 SUR of the fourth individual obtained after pretreated with methylphenidate HCl; a fourth [$^{99m}$Tc]TRODAT-1 SUR of the fourth individual obtained after pretreated with fluoxetine; a third [$^{123}$I]ADAM SUR of the fourth individual obtained after pretreated with methylphenidate HCl; and a fourth [$^{123}$I]ADAM SUR of the fourth individual obtained after pretreated with fluoxetine, and comparing the third and the fourth [$^{99m}$Tc]TRODAT-1 SURs with the second [$^{99m}$Tc]TRODAT-1 SUR and comparing the third and the fourth [$^{123}$I]ADAM SURs with the second [$^{123}$I]ADAM SUR to evaluate effects of methylphenidate HCl and fluoxetine on diagnosing anomalies of dopamine and serotonin in primates through SPECT. Accordingly, a novel method of nuclear medical photography using dual-isotopes is obtained.

BRIEF DESCRIPTIONS OF THE DRAWINGS

The present disclosure will be better understood from the following detailed description of the preferred embodiment according to the present disclosure, taken in conjunction with the accompanying drawings, in which FIG. 1 is the flow view showing the preferred embodiment according to the present disclosure;

DESCRIPTION OF THE PREFERRED EMBODIMENT

The following description of the preferred embodiment is provided to understand the features and the structures of the present disclosure.

Figure 1:
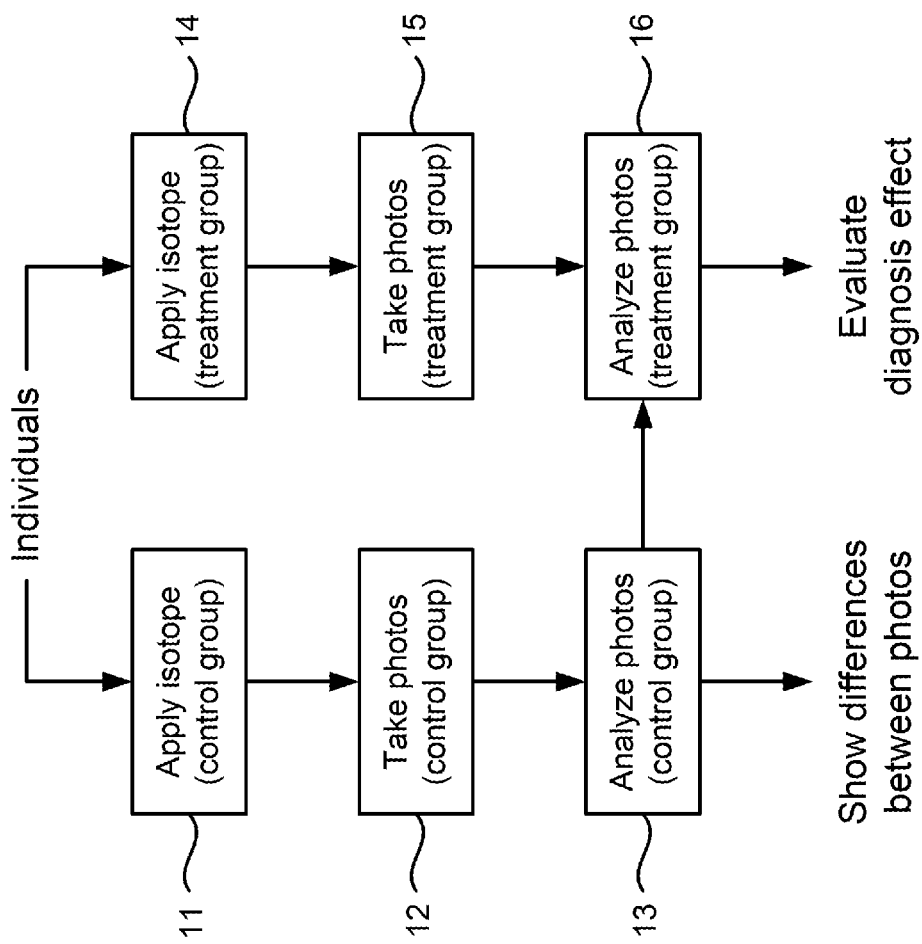
Figure 2:
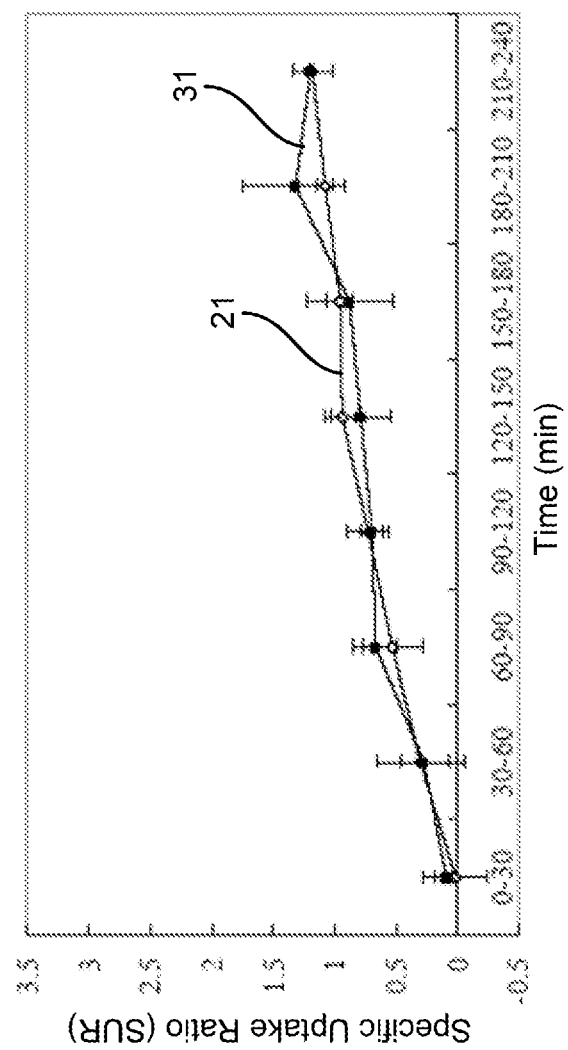
FIG. 2 is the view showing [$^{123}$I]ADAM SBR curves for serotonin transporters of striatum applied with the single-isotope of [$^{123}$I]ADAM and the dual-isotopes.
Figure 3:
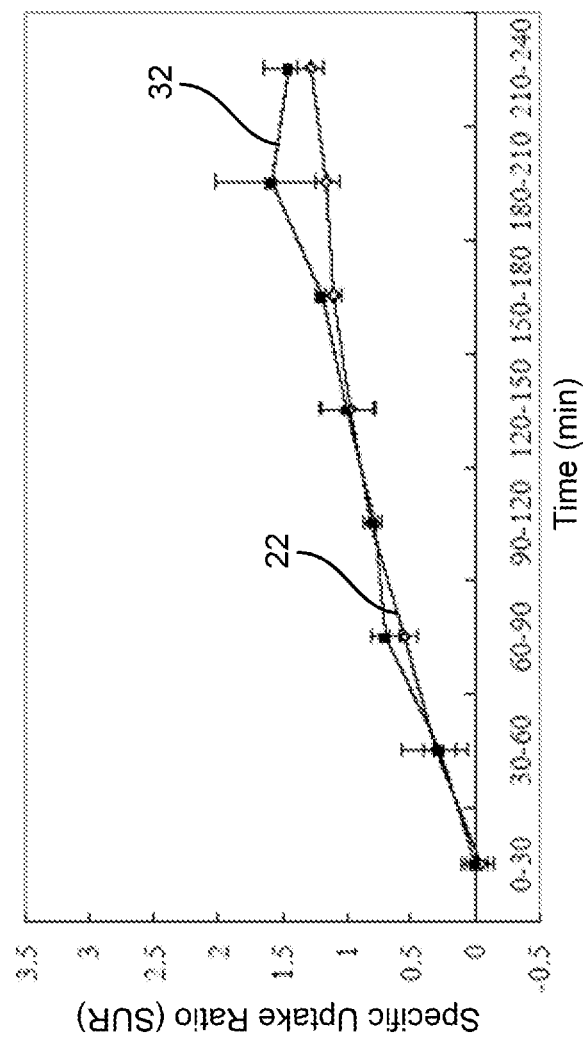
FIG. 3 is the view showing [$^{123}$I]ADAM SBR curves for serotonin transporters of thalamus applied with the single-isotope of [$^{123}$I]ADAM and the dual-isotopes.
Figure 4:
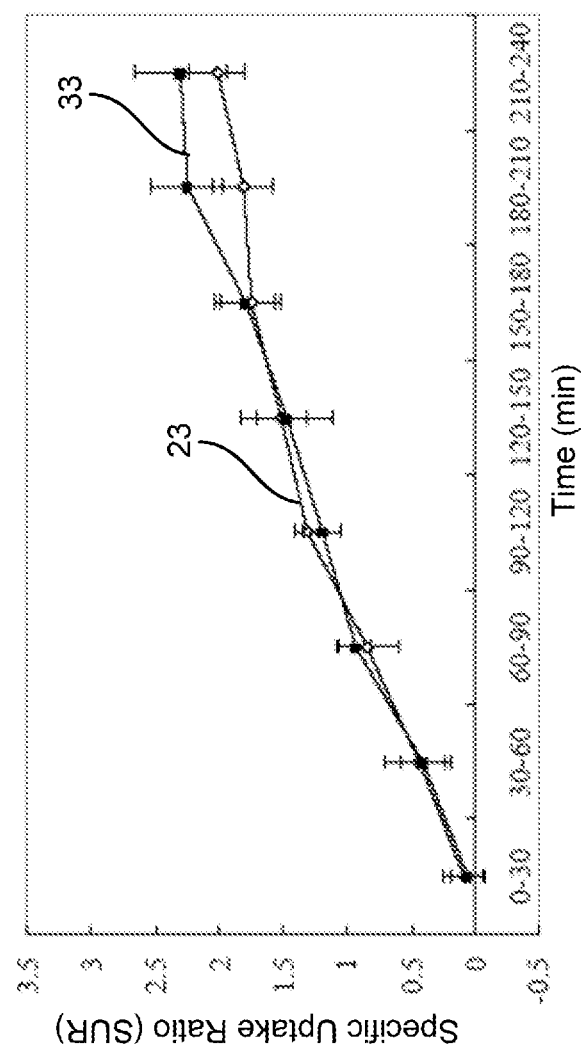
FIG. 4 is the view showing [$^{123}$I]ADAM SBR curves for serotonin transporters of midbrain applied with the single-isotope of [$^{123}$I]ADAM and the dual-isotopes.
Figure 5:
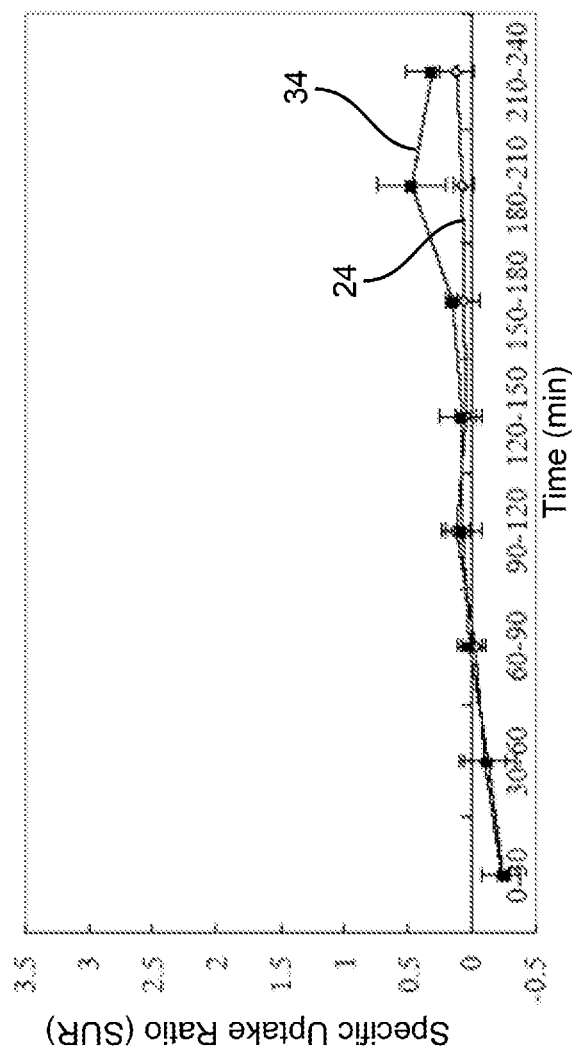
FIG. 5 is the view showing [$^{123}$I]ADAM SBR curves for serotonin transporters of frontal cortex applied with the single-isotope of [$^{123}$I]ADAM and the dual-isotopes.

Please refer to FIG. 1, which is a flow view showing a preferred embodiment according to the present disclosure. As shown in the figure, the present disclosure is a method of nuclear medical photography using dual-isotopes, where effect of using dual isotopes on diagnosing anomalies of dopamine and serotonin in primate's brain is evaluated. The present disclosure comprises the following steps:

(a) Obtaining control group 11: A control group is obtained, comprising at least one first individual applied with an imaging agent of single-isotope of [$^{99m}$Tc]TRODAT-1 for dopamine transporter; at least one second individual applied with an imaging agent of single-isotope of [$^{123}$I]ADAM for serotonin transporter; and at least one third individual applied with imaging agents of dual-isotopes of [$^{99m}$Tc]TRODAT-1 and [$^{123}$I]ADAM. Therein, the individuals are non-human primates, like Macaca Cyclopis.

(b) Taking photos for control group 12: Photos of the first to the third individuals in the control group are taken through single photon emission computed tomography (SPECT). Therein, on taking the photo of the first individual applied with the single-isotope of [$^{99m}$Tc]TRODAT-1, 90 mg/ml of KClO$_4$ is applied to the first individual at first; and, then, after 20 minutes, 740 MBq (20 mCi) of [$^{99m}$Tc]TRODAT-1 is injected from intravenous. After [$^{99m}$Tc]TRODAT-1 is injected, a SPECT device equipped with dual-headed gamma cameras (Hawkeye, Millennium VG, General Elecral Medical System, Milwaukee, Wis. USA) coordinated with fan-beam collimators is used to take photos, where 15 dynamic sequence of brain images are taken during 30 minutes (2 min/frame). Therein, an energy window is set between 126 Kev and 154 Kev; data of 128×128 pixel-matrice are fetched; each photo are enlarged for 1.6 times; a photo is taken for each 3° from 360°; and, each of the two detectors is responsible for taking photos for 180°. After data are collected and processed through Metz filter with attenuation calibration, three three-dimensional (3D) photos of coronal, sagittal and transaxial sections are formed. On taking the photo of the second individual applied with the single-isotope of [$^{123}$I]ADAM, 185 MBq (5 mCi) of [$^{123}$I]ADAM is injected from intravenous; and, an energy window is set between 143 Kev and 175 Kev. On taking the photo of the third individual applied with the dual-isotopes, 90 mg/ml of KClO$_4$ is applied to the first individual at first; and, after 20 minutes, 740 MBq (20 mCi) of [$^{99m}$Tc]TRODAT-1 and 185 MBq (5 mCi) of [$^{123}$I]ADAM are injected from intravenous almost simultaneously. Therein, an energy window for [$^{99m}$Tc]TRODAT-1 is set between 129 Kev and 151 Kev and another energy window for [$^{123}$I]ADAM is set between 159 Kev and 175 Kev.

(c) Analyzing photos of control group 13: Magnetic resonance imaging (MRI) photos of the first to the third individuals are taken to provide reference information for the following analysis:

(c1) Analysis on [$^{123}$I]ADAM: The photo of the first individual applied with the single-isotope of [$^{123}$I]ADAM obtained in step (b) are processed through visual interpretation to pick out regions of interest (ROI) abundant in serotonin transporter, like midbrain, thalamus, striatum and frontal cortex; and a region lack of serotonin transporter, like cerebellum, is set as background. Mean counts per pixel (MCPP) of the ROIs are deducted with MCPPs of the background and then are divided by the MCPPs of the background to figure out a specific uptake ratios (SUR) of the single-isotope of [$^{123}$I]ADAM.

(c2) Analysis on [$^{99m}$Tc]TRODAT-1: In the photo of the second individual applied with the single-isotope of [$^{99m}$Tc]TRODAT-1 obtained in step (b), ROIs abundant in serotonin transporter, like striatum, are picked out; and cerebellum is set as background. MCPPs of the ROIs are deducted with MCPPs of the background and then are divided by the MCPPs of the background to figure out an SUR of the single-isotope of [$^{99m}$Tc]TRODAT-1.

(c3) Analysis on dual-isotopes: The photo of the third individual applied with the dual-isotopes of [$^{123}$I]ADAM and [$^{99m}$Tc]TRODAT-1 obtained in step (b) are processed through visual interpretation to figure out an SUR of [$^{99m}$Tc]TRODAT-1 in striatum and an SUR of [$^{123}$I]ADAM in midbrain, thalamus, striatum and frontal cortex. The SURs for the dual-isotopes are separately compared with the SUR of [$^{123}$I]ADAM figured out in step (c1) and the SUR of [$^{99m}$Tc]TRODAT-1 figured out in step (c2) to evaluate differences in between.

Therein, the data obtained for the dual-isotopes in step (c3) are also used to compare with data for a treatment group obtained in the following steps.

(d) Obtaining treatment group 14: After being pretreated with a blocking agent of methylphenidate HCl for dopamine transporter and a blocking agent of fluoxetine for serotonin transporter separately, a fourth individual is applied with the dual-isotopes to obtain a treatment group. Therein, 1 mg/kg of methylphenidate HCl is used for pretreatment 10 minutes before [$^{99m}$Tc]TRODAT-1 is injected into the fourth individual; and, 20 mg/Tab. of fluoxetine is used for pretreatment at 16 and 20 hours separately before [$^{123}$I]ADAM is injected into the fourth individual.

(e) Taking photos for treatment group 15: Through SPECT, a photo of the fourth individual applied with the dual-isotopes is taken after pretreating the fourth individual with methylphenidate HCl, and a photo of the fourth individual applied with the dual-isotopes is taken after pretreating the fourth individual with fluoxetine.

(f) Analyzing photos of treatment group 16: The photos obtained in step (e) are processed through visual interpretation to figure out [$^{99m}$Tc]TRODAT-1 SURs in striatum and [$^{123}$I]ADAM SURs in midbrain, thalamus, striatum and frontal cortex of the fourth individual obtained after being applied with methylphenidate HCl or fluoxetine. Then, the photos obtained in step (e) and the SURs figured out in this step are compared with the photos of the third individual obtained in step (b) and the SURs figured out in step (c3). By the comparison, effects of methylphenidate HCl and fluoxetine on diagnosing anomalies of dopamine and serotonin in primates are evaluated through SPECT.

Therein, in step (b) and step (e), a SPECT device equipped with dual-headed gamma cameras is used to take photos of dopamine transporter and serotonin transporter in brains of the individuals with coordination of fan-beam collimators.

In the control group, each individual is taken a SPECT photo for the single-isotope of [$^{123}$I]ADAM, a SPECT photo for the single-isotope of [$^{99m}$Tc]TRODAT-1 and a SPECT photo for the dual-isotopes, where each individual is thus taken three photos with a two-week duration between every two photos. In the treatment group, for processing SPECT, each individual is at first pretreated with fluoxetine and then is applied with the dual-isotopes; and is pretreated with methylphenidate HCl and then is applied with the dual-isotopes. Thus, each individual is processed through two pretreatments with duration depending on the blocking agent used.

Please refer to FIG. 2 to FIG. 5, which are views showing [$^{123}$I]ADAM SBR curves for serotonin transporters of striatum, thalamus, midbrain and frontal cortex applied with a single-isotope of [$^{123}$I]ADAM and dual-isotopes separately. As shown in the figures, 180 to 210 minutes after isotopes are injected, photos of individuals applied with a single-isotope of [$^{123}$I]ADAM and photos of individuals applied with dual-isotopes of [$^{123}$I]ADAM and [$^{99m}$Tc]TRODAT-1 are compared. It is found that [$^{123}$I]ADAM is bound to regions abundant in serotonin transporter, like midbrain, thalamus and striatum; and that there is no big difference between photos of the individuals applied with the single-isotope of [$^{123}$I]ADAM or the dual-isotopes.

In FIG. 2 to FIG. 5, the first to the fourth ratio curves 21~4 respectively are curves of specific binding ratio (SBR) of [$^{123}$I]ADAM ([$^{123}$I]ADAM SBR curves) of striatum, thalamus, midbrain and frontal cortex of the individual applied with the single-isotope of [$^{123}$I]ADAM; and the sixth to the ninth ratio curves 31~34 respectively are the [$^{123}$I]ADAM SBR curves of striatum, thalamus, midbrain and frontal cortex of the individual applied with the dual-isotopes. By comparing the [$^{123}$I]ADAM SURs, the SURs of the individual applied with the single-isotope has no big difference to the SURs of the individual applied with the dual-isotopes, where those SURs are increased following time flows.

Figure 6:
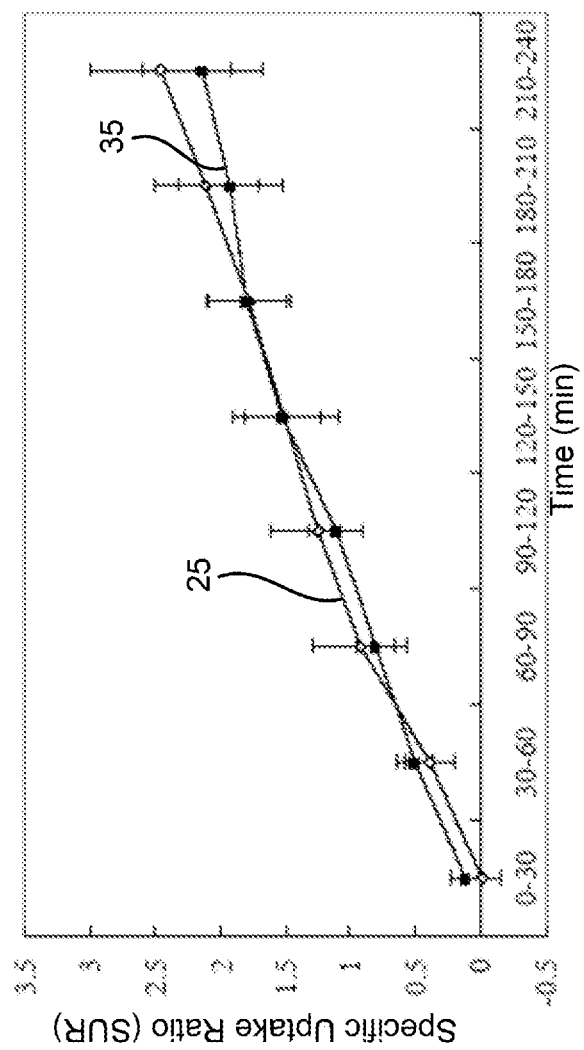
FIG. 6 is the view showing [$^{99m}$Tc]TRODAT-1 SBR curves for dopamine transporters of striatum applied with the single-isotope of [$^{99m}$Tc]TRODAT-1 and the dual-isotopes.
Figure 7:
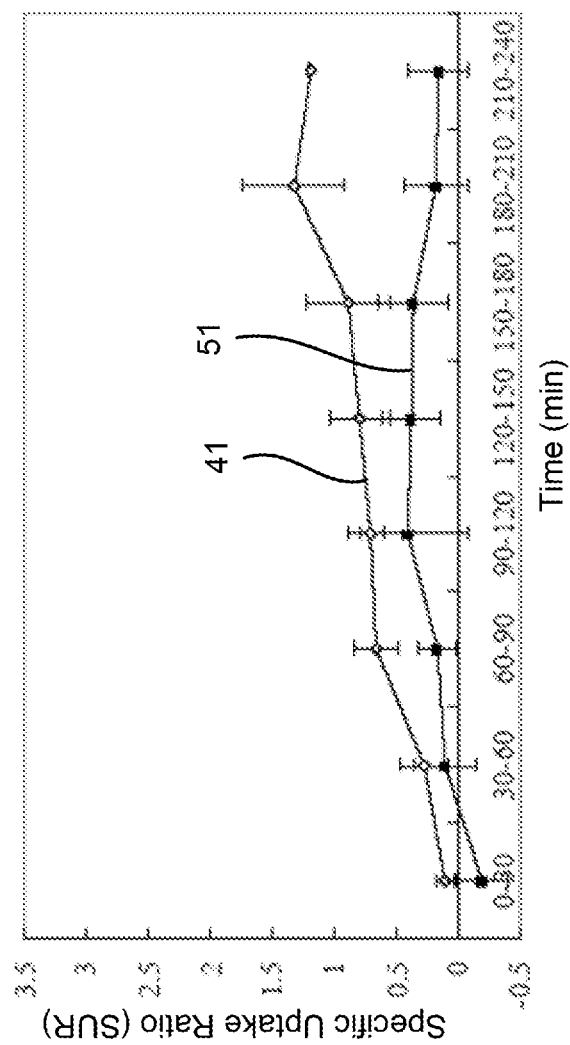
FIG. 7 is the view showing [$^{123}$I]ADAM SBR curves for serotonin transporters of striatum applied with the dual-isotopes before and after pretreated with fluoxetine.
Figure 8:
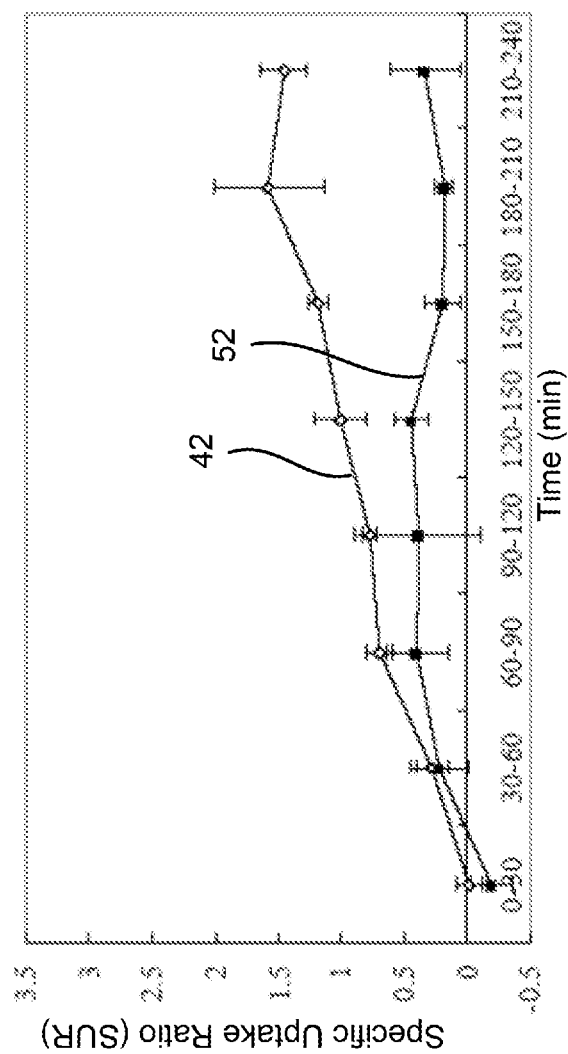
FIG. 8 is the view showing [$^{123}$I]ADAM SBR curves for serotonin transporters of thalamus applied with the dual-isotopes before and after pretreated with fluoxetine.
Figure 9:
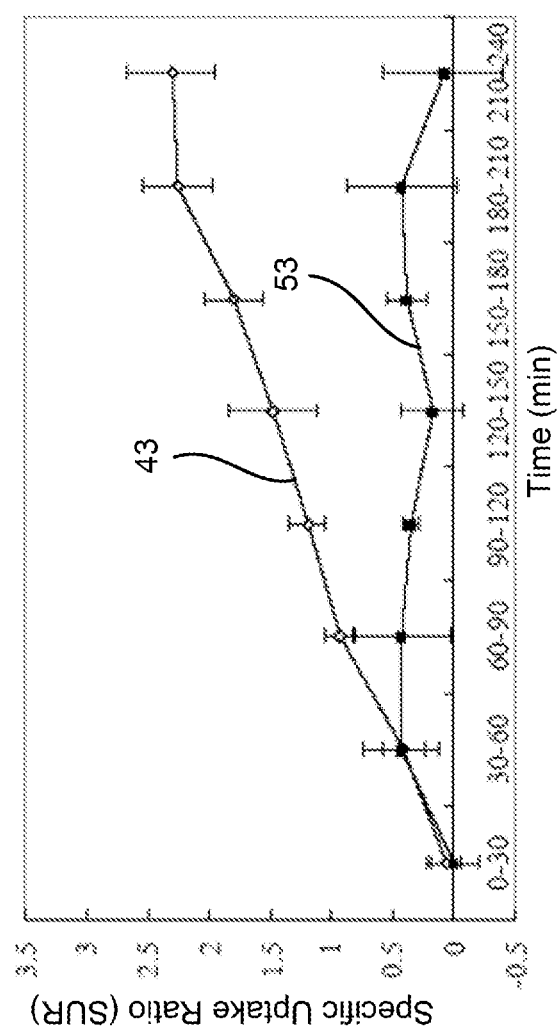
FIG. 9 is the view showing [$^{123}$I]ADAM SBR curves for serotonin transporters of midbrain applied with the dual-isotopes before and after pretreated with fluoxetine.
Figure 10:
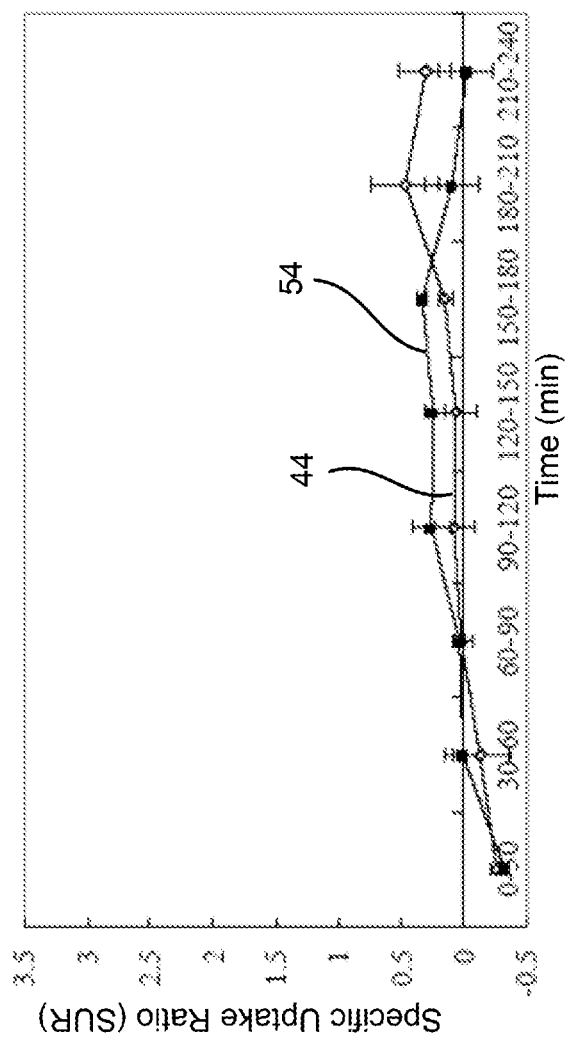
FIG. 10 is the view showing [$^{123}$I]ADAM SBR curves for serotonin transporters of frontal cortex applied with the dual-isotopes before and after pretreated with fluoxetine.

Please refer to FIG. 6, which is a view showing [$^{99m}$Tc]TRODAT-1 SBR curves for dopamine transporters of striatum applied with a single-isotope of [$^{99m}$Tc]TRODAT-1 and dual-isotopes. As shown in the figure, 180 to 210 minutes after isotopes are injected, photos of individuals applied with a single-isotope of [$^{99m}$Tc]TRODAT-1 and photos of individuals applied with dual-isotopes of [$^{123}$I]ADAM and [$^{99m}$Tc]TRODAT-1 are compared. It is found that a [$^{99m}$Tc]TRODAT-1 SUR of striatum of the individual applied with the single-isotope of [$^{99m}$Tc]TRODAT-1 has no big difference to a [$^{99m}$Tc]TRODAT-1 SUR of striatum of the individual applied with the dual-isotopes of [$^{123}$I]ADAM and [$^{99m}$Tc]TRODAT-1. Therein, a fifth ratio curve 25 shows an SBR curve of [$^{99m}$Tc]TRODAT-1 of striatum of the individual applied with the single-isotope of [$^{99m}$Tc]TRODAT-1; and, a tenth ratio curve 35 shows an SBR curve of [$^{99m}$Tc]TRODAT-1 of striatum of the individual applied with the dual-isotopes of [$^{99m}$Tc]TRODAT-1 and [$^{123}$I]ADAM. Thus, applications with dual-isotopes are fit for SPECT.

Please refer to FIG. 7 to FIG. 10, which are views showing [$^{123}$I]ADAM SBR curves for serotonin transporters of striatum, thalamus, midbrain and frontal cortex applied with the dual-isotopes before and after pretreated with fluoxetine, respectively. As shown in the figures, 180 to 210 minutes after dual-isotopes of [$^{123}$I]ADAM and [$^{99m}$Tc]TRODAT-1 are injected, photos of individuals applied with the dual-isotopes after pretreated with fluoxetine show that uptake of [$^{123}$I]ADAM in midbrain, striatum and thalamus of the individuals are totally blocked.

In FIG. 7 to FIG. 10, an eleventh to a fourteenth ratio curves 41~44 respectively are [$^{123}$I]ADAM SBR curves of striatum, thalamus, midbrain and frontal cortex of the individual applied with the dual-isotopes; and a sixteenth to a nineteenth ratio curves 31~34 respectively are [$^{123}$I]ADAM SBR curves of striatum, thalamus, midbrain and frontal cortex of the individual applied with the dual-isotopes after pretreated with fluoxetine for 16 hours. By comparing the SURs, the [$^{123}$I]ADAM SURs of striatum, thalamus and midbrain of the individuals applied with the dual-isotopes after pretreated with fluoxetine for 16 hours are lowered. But, the [$^{123}$I]ADAM SURs of frontal cortex of the same individuals have no big change.

Figure 11:
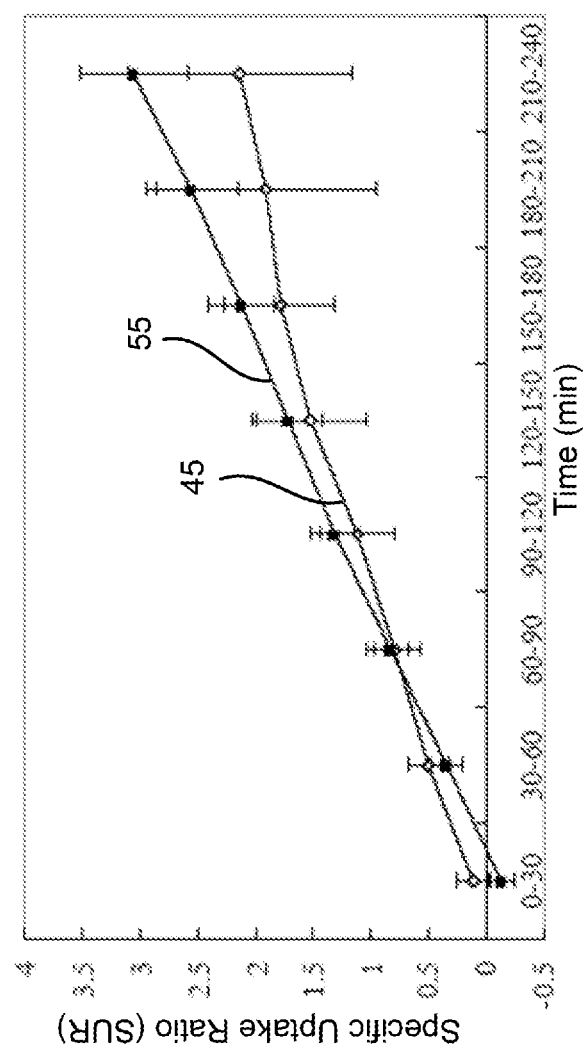
FIG. 11 is the view showing [$^{99m}$Tc]TRODAT-1 SBR curves for dopamine transporters of striatum applied with the dual-isotopes before and after pretreated with fluoxetine.
Figure 12:
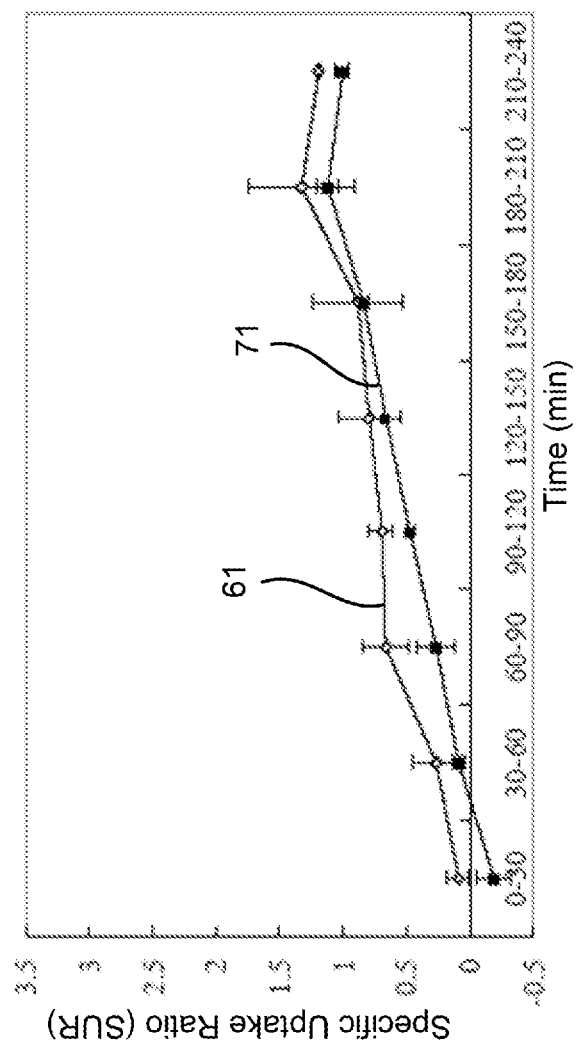
FIG. 12 is the view showing [$^{123}$I]ADAM SBR curves for serotonin transporters of striatum applied with the dual-isotopes before and after pretreated with methylphenidate HCl.
Figure 13:
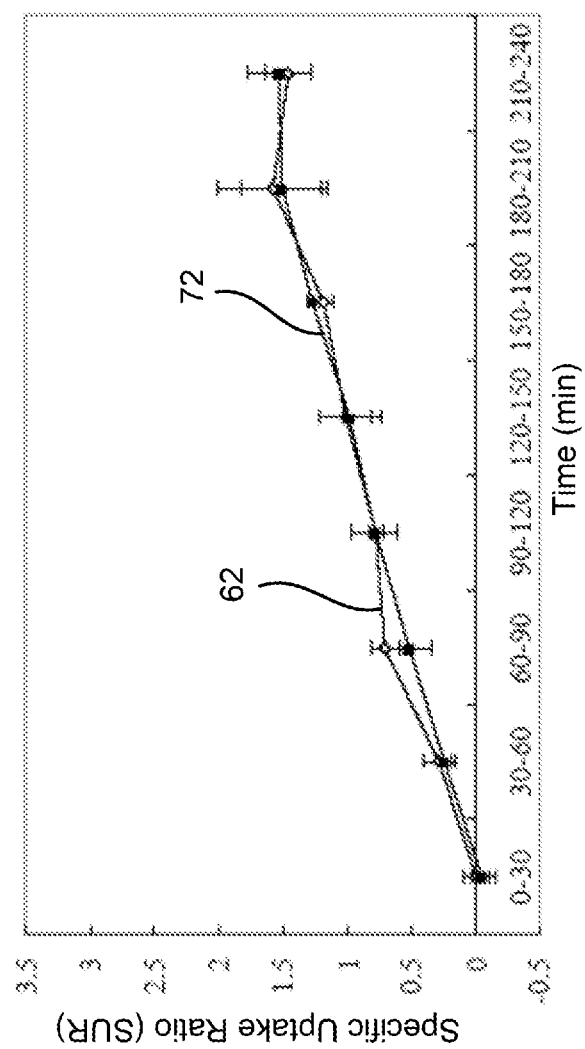
FIG. 13 is the view showing [$^{123}$I]ADAM SBR curves for serotonin transporters of thalamus applied with the dual-isotopes before and after pretreated with methylphenidate HCl.
Figure 14:
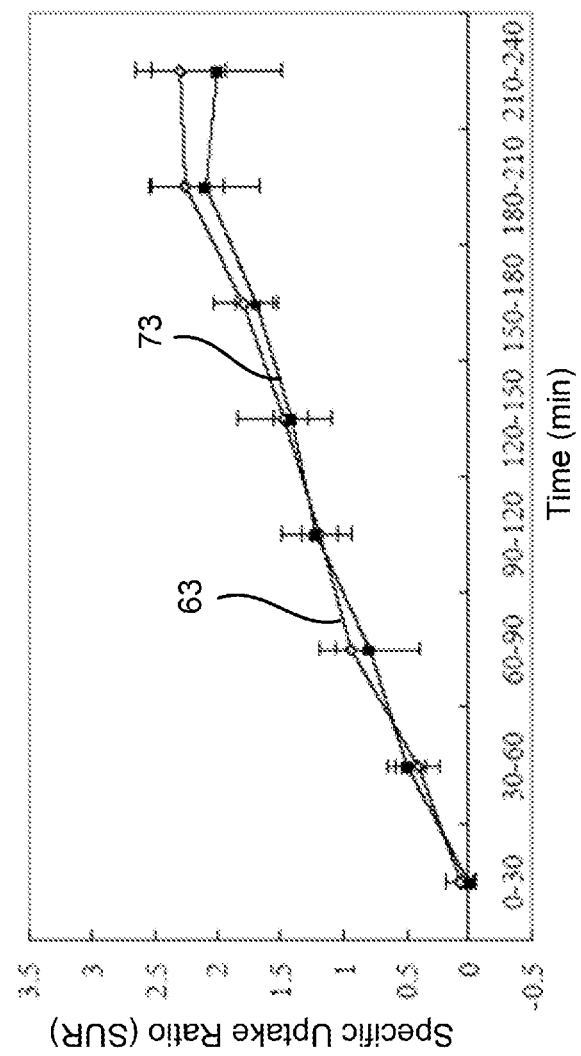
FIG. 14 is the view showing [$^{123}$I]ADAM SBR curves for serotonin transporters of midbrain applied with the dual-isotopes before and after pretreated with methylphenidate HCl.
Figure 15:
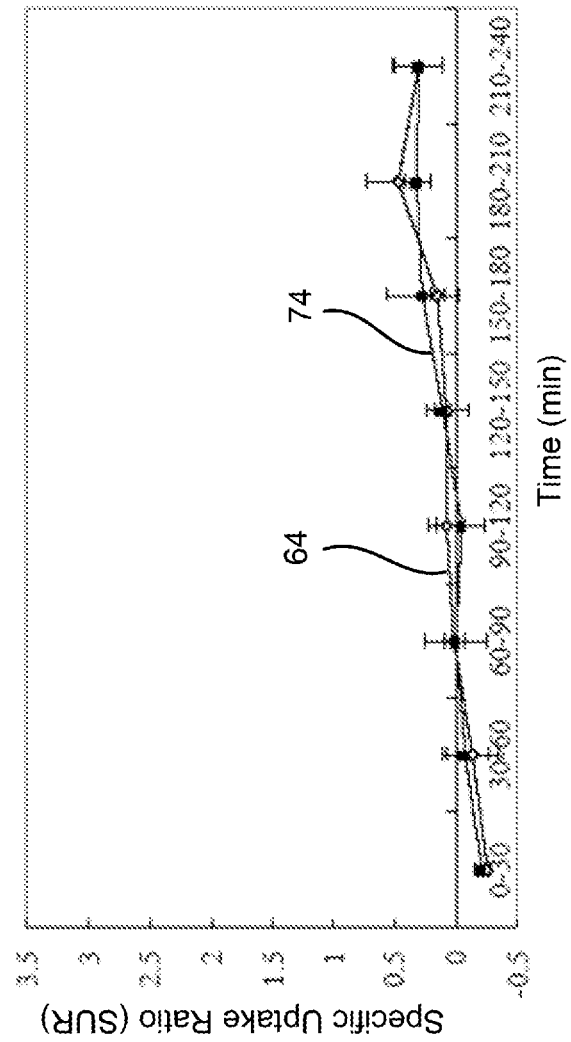
FIG. 15 is the view showing [$^{123}$I]ADAM SBR curves for serotonin transporters of frontal cortex applied with the dual-isotopes before and after pretreated with methylphenidate HCl.

Please refer to FIG. 11, which is a view showing [$^{99m}$Tc]TRODAT-1 SBR curves for dopamine transporters of striatum applied with dual-isotopes before and after pretreated with fluoxetine. As shown in the figure, 180 to 210 minutes after dual-isotopes of [$^{99m}$Tc]TRODAT-1 and [$^{123}$I]ADAM are injected, photos of individuals applied with the dual-isotopes after pretreated with fluoxetine for 16 hours show that [$^{99m}$Tc]TRODAT-1 SURs have no big changes in striatum. Therein, a twentieth ratio curve 55 shows [$^{99m}$Tc]TRODAT-1 SURs of striatum of the individuals applied with the dual-isotopes after pretreated with fluoxetine for 16 hours.

Please refer to FIG. 12 to FIG. 15, which are views showing [$^{123}$I]ADAM SBR curves for serotonin transporters of striatum, thalamus, midbrain and frontal cortex applied with the dual-isotopes before and after pretreated with methylphenidate HCl, respectively. As shown in the figures, 180 to 210 minutes after dual-isotopes of [$^{99m}$Tc]TRODAT-1 and [$^{123}$I]ADAM are injected, photos of individuals applied with the dual-isotopes after pretreated with methylphenidate HCl show that uptakes of [$^{123}$I]ADAM in midbrain, striatum, thalamus and frontal cortex of the individuals pretreated with methylphenidate HCl have no big difference to those uptakes of [$^{123}$I]ADAM in midbrain, striatum, thalamus and frontal cortex of individuals not pretreated with methylphenidate HCl.

In FIG. 12 to FIG. 15, the twenty-first to the twenty-fourth ratio curves 61~64 respectively are [$^{123}$I]ADAM SBR curves of striatum, thalamus, midbrain and frontal cortex of the individuals applied with the dual-isotopes; and, the twenty-sixth to the twenty-ninth ratio curves 71~74 respectively are [$^{123}$I]ADAM SBR curves of striatum, thalamus, midbrain and frontal cortex of the individuals applied with the dual-isotopes after pretreated with methylphenidate HCl. By comparing the SURs, the [$^{123}$I]ADAM SURs of striatum, thalamus and midbrain of the individuals applied with the dual-isotopes after pretreated with methylphenidate HCl have no big changes.

Figure 16:
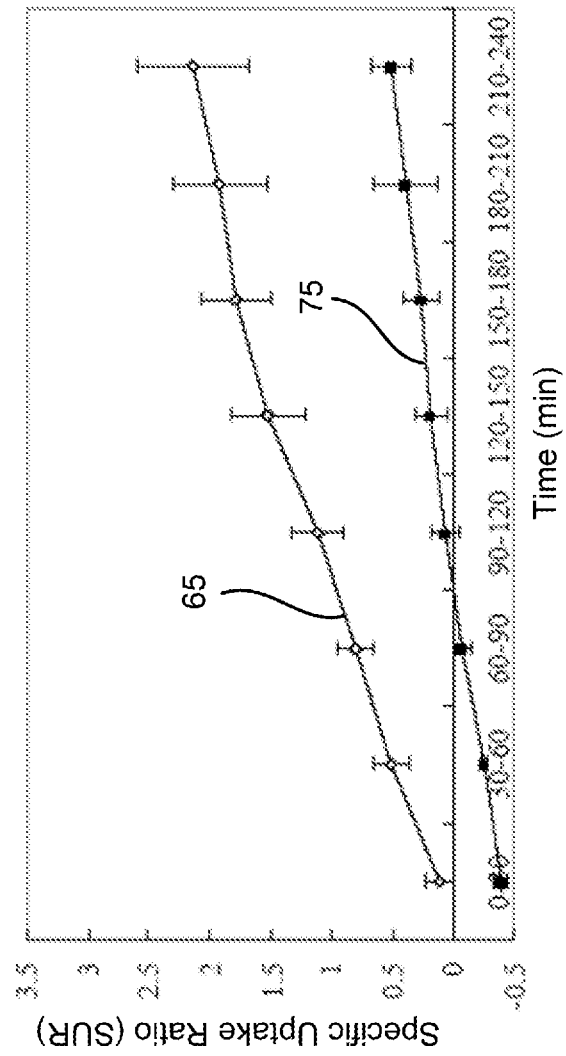
FIG. 16 is the view showing [$^{99m}$Tc]TRODAT-1 SBR curves for dopamine transporters of striatum applied with the dual-isotopes before and after pretreated with methylphenidate HCl.

Please refer to FIG. 16, which is a view showing [$^{99m}$Tc]TRODAT-1 SBR curves for dopamine transporters of striatum applied with the dual-isotopes before and after pretreated with methylphenidate HCl. As shown in the figure, 180 to 210 minutes after dual-isotopes of [$^{99m}$Tc]TRODAT-1 and [$^{123}$I]ADAM are injected, photos of individuals applied with the dual-isotopes after pretreated with methylphenidate HCl show that [$^{99m}$Tc]TRODAT-1 SURs is greatly lowered in striatum. Therein, a twenty-fifth ratio curve 65 shows [$^{99m}$Tc]TRODAT-1 SURs of striatum of the individuals applied with the dual-isotopes; and a thirtieth ratio curve 75 shows [$^{99m}$Tc]TRODAT-1 SURs of striatum of the individuals applied with the dual-isotopes after pretreated with methylphenidate HCl.

Conclusively, the treatment group pretreated with methylphenidate HCl or fluoxetine is applied with dual-isotopes and then are taken photos through SPECT. As shown in the photos, uptakes of [$^{123}$I]ADAM in midbrain, thalamus, striatum and frontal cortex are blocked after pretreated with fluoxetine for 16 hours; and the same is SURs of [$^{123}$I]ADAM. In addition, after the individuals in the treatment group are pretreated with fluoxetine for 16 hours, since fluoxetine is mainly functioned on serotonin transporter, uptakes of [$^{99m}$Tc]TRODAT-1 of striatum of the individuals in the treatment group have no big difference to that of individuals not pretreated with fluoxetine. Hence, it is proved that even after pretreated with fluoxetine, SPECT photos of individuals applied with dual-isotopes can show anomalies of serotonin transporters.

In the other hand, by comparing the [$^{123}$I]ADAM photos of the individuals pretreated with methylphenidate HCl with the [$^{123}$I]ADAM photos of the individuals not pretreated with methylphenidate HCl, it shows that specific uptakes of [$^{123}$I]ADAM of midbrain, thalamus, striatum and frontal cortex have no big changes; but, uptakes of [$^{99m}$Tc]TRODAT-1 of striatum of the individuals applied with the dual-isotopes after pretreated with methylphenidate HCl is obviously reduced. It means that [$^{99m}$Tc]TRODAT-1 in the dual-isotopes can compete with methylphenidate HCl with a very high specifity; and that [$^{123}$I]ADAM in the dual-isotopes still has normal function to serotonin. Hence, methylphenidate HCl can be used for evaluating effect of methylphenidate HCl pretreated on individuals before applied with dual-isotopes of [$^{123}$I]ADAM and [$^{99m}$Tc]TRODAT-1; and, specifity on dopamine transporter and distribution of dopamine transporter can be clearly obtained for detecting abnormality on dopamine transporter.

In the present disclosure, on comparing the SPECT photos applied with a single-isotope or dual-isotopes, quality of the photos and SURs are very similar. Therefore, SPECT can be used on individuals applied with the dual-isotopes to distinguish images of dopamine transporter and serotonin transporter. Besides, anomaly of dopamine transporter can be distinguished from anomaly of serotonin transporter in the SPECT photos of the individuals applied with the dual-isotopes after pretreated with methylphenidate HCl or fluoxetine. Thus, SPECT using dual-isotopes of [$^{99m}$Tc]TRODAT-1 and [$^{123}$I]ADAM is an effective method for diagnosing anomalies of dopamine and serotonin system in human brain.

To sum up, the present disclosure is a method of nuclear medical photography using dual-isotopes, where photos of dopamine and serotonin system can be simultaneously obtained in one examination to save cost and labor for two examinations and uses of SPECT.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A method of nuclear medical photography using dual-isotopes, comprising steps of:
   (a) obtaining a control group, comprising
   at least one first individual applied with an imaging agent of single-isotope of [$^{99m}$Tc]TRODAT-1 for dopamine transporter;
   at least one second individual applied with an imaging agent of single-isotope of [$^{123}$I]ADAM for serotonin transporter; and
   at least one third individual applied with imaging agents of dual-isotopes of [$^{99m}$Tc]TRODAT-1 and [$^{123}$I]ADAM;
   (b) obtaining photos of said first to said third individuals in said control group through single photon emission computed tomography (SPECT),
   wherein, on obtaining said photo of said first individual through SPECT, an energy window between 126 Kev and 154 Kev is set for said single-isotope of [$^{99m}$Tc]TRODAT-1; and
   wherein, on obtaining said photo of said third individual through SPECT, an energy window between 129 Kev and 151 Kev is set for [$^{99m}$Tc]TRODAT-1 in said dual-isotopes;
   (c) processing said photos obtained in step (b) through visual interpretation to obtain a first specific uptake ratio (SUR) of [$^{99m}$Tc]TRODAT-1 ([$^{99m}$Tc]TRODAT-1 SUR) of said first individual;
   a first SUR of [$^{123}$I]ADAM ([$^{123}$I]ADAM SUR) of said second individual;
   a second [$^{99m}$Tc]TRODAT-1 SUR of said third individual; and
   a second [$^{123}$I]ADAM SUR of said third individual, and comparing said second [$^{99m}$Tc]TRODAT-1 SUR of said third individual and said second [$^{123}$I]ADAM SUR of said third individual with said first [$^{99m}$Tc]TRODAT-1 SUR of said first individual and said first [$^{123}$I]ADAM SUR of said first individual;
   (d) obtaining a treatment group, comprising
   at least one fourth individual applied with said dual-isotopes of [$^{99m}$Tc]TRODAT-1 and [$^{123}$I]ADAM after pretreating said fourth individual with a blocking agent of methylphenidate HCl for dopamine transporter and a blocking agent of fluoxetine for serotonin transporter separately;
   (e) obtaining photos of said fourth individual in said treatment group through SPECT after pretreating said fourth individual with methylphenidate HCl and Fluoxetine separately; and
   (f) processing said photos obtained in step (e) through visual interpretation to obtain a third [$^{99m}$Tc]TRODAT-1 SUR of said fourth individual obtained after being pretreated with methylphenidate HCl;

a fourth [$^{99m}$Tc]TRODAT-1 SUR of said fourth individual obtained after being pretreated with fluoxetine;

a third [$^{123}$I]ADAM SUR of said fourth individual obtained after being pretreated with methylphenidate HCl; and a fourth [$^{123}$I]ADAM SUR of said fourth individual obtained after being pretreated with fluoxetine, and comparing said third and said fourth [$^{99m}$Tc]TRODAT-1 SURs of said fourth individual with said second [$^{99m}$Tc]TRODAT-1 SUR of said third individual and comparing said third and said fourth [$^{123}$I]ADAM SURs of said fourth individual with said second [$^{123}$I]ADAM SUR of said third individual to evaluate effects of methylphenidate HCl and fluoxetine on diagnosing anomalies of dopamine and serotonin in primates through SPECT.

2. The method according to claim 1,
wherein said first to said sixth individuals are non-human primates.

3. The method according to claim 1,
wherein, in step (b) and step (e), said photos are taken for dopamine transporter and serotonin transporter in said first to said sixth individuals through SPECT equipped with dual-headed gamma cameras coordinated with fan-beam collimators.

* * * * *